United States Patent [19]
Micheloni et al.

[11] Patent Number: 5,487,188
[45] Date of Patent: Jan. 30, 1996

[54] GLOVE WITH MEANS FOR PROTECTING THE LIGAMENTS AND ARTICULATIONS OF THE HAND

[76] Inventors: Walter Micheloni, Via Piavanini 30;
Fabrizio Giugni, Via Caselle 13, both of 23100 Albosaggia (Sondrio), Italy;
Georg Ahlbaumer, Via Arona 34, 7500 St. Moritz, Switzerland

[21] Appl. No.: 263,512

[22] Filed: Jun. 22, 1994

[30] Foreign Application Priority Data

Aug. 24, 1993 [IT] Italy .................. MI93A1846

[51] Int. Cl.$^6$ .................. A41D 13/08
[52] U.S. Cl. .................. 2/16; 2/159; 2/160; 2/161.1
[58] Field of Search .................. 2/260, 261.1, 16, 2/17, 159, 160, 161.1, 161.5, 161.6, 162, 166, 167, 170

[56] References Cited

U.S. PATENT DOCUMENTS

| | | | |
|---|---|---|---|
| 3,038,723 | 6/1962 | Bergendorf | 2/161.1 |
| 4,524,464 | 6/1985 | Primiano et al. | 2/161.1 |
| 4,881,275 | 11/1989 | Lazaies et al. | 2/161.1 |
| 5,313,667 | 5/1994 | Levine | 2/160 |

*Primary Examiner*—C. D. Crowder
*Assistant Examiner*—Larry D. Worrell, Jr.
*Attorney, Agent, or Firm*—Bucknam and Archer

[57] ABSTRACT

A glove for protecting the ligaments, articulations and bones of the hand, has a glove body, to which is associated a plate for protecting the hand palm, at the proximal region of the forearm, which is provided, at one end, with an annular element encompassing the attachment region of the thumb. To the plate there is articulated a shield which is engaged with the forearm, tie-straps being moreover provided connecting the fingers of the glove with the plate.

10 Claims, 3 Drawing Sheets

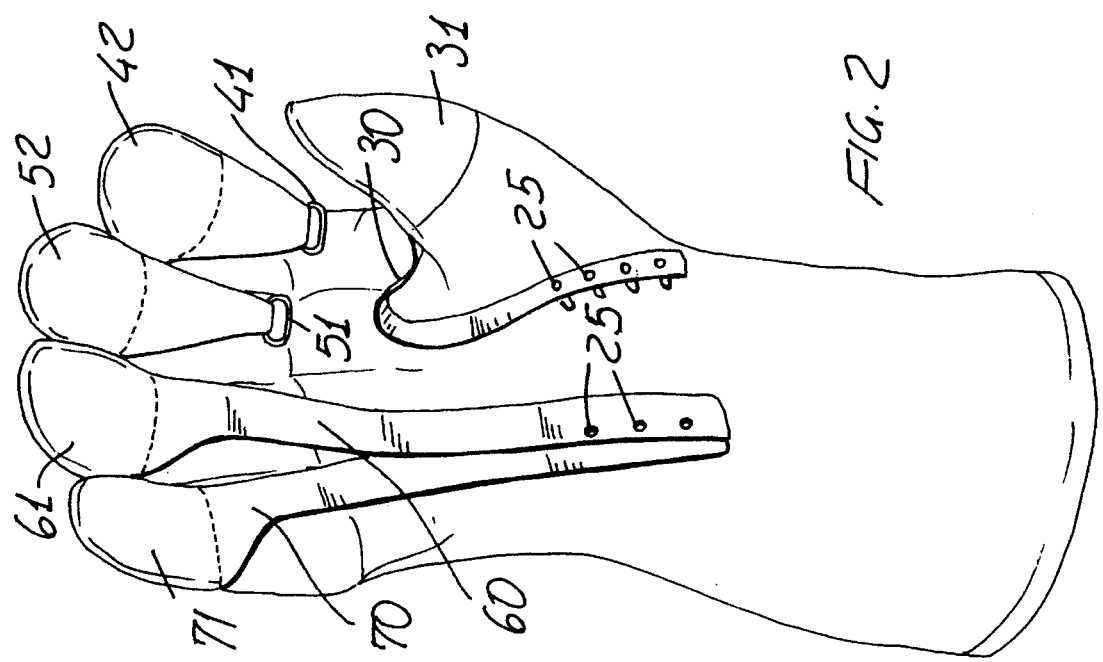
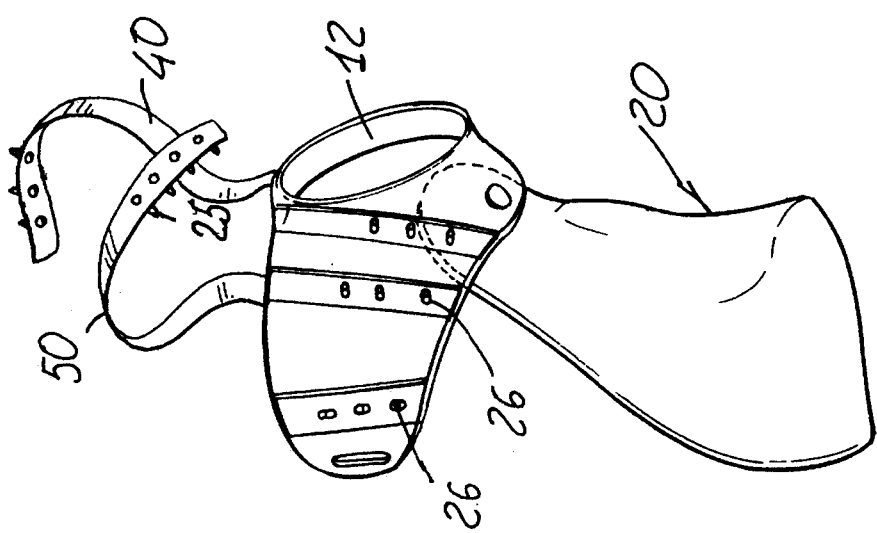

GLOVE WITH MEANS FOR PROTECTING THE LIGAMENTS AND ARTICULATIONS OF THE HAND

BACKGROUND OF THE INVENTION

The present invention relates to a glove construction, provided with means for protecting the ligaments and articulations of the hand.

There are already available on the market several types of protective gloves, for very different applications, which gloves, however, usually exclusively protect the surface of the hand by suitable materials or paddings, for cushioning impacts.

In particular, the sport use gloves, such as, for example, the ski gloves, are made of a padding material which, at first, has a thermal protective function and, moreover, being provided for protecting the user hand against impacts.

However, these prior gloves have not been found to properly protect the ligaments and articulations of the hand, for example as a skier falls and, in the case of violent falling, frequently occur lesions of the ligaments and dislocations of the hand articulations, as well as fractures of the hand bones.

In fact, as a skier falls against the ground, he/she usually bears the palm of his/her hand against the soil, thereby causing the mentioned lesions of the ligaments or bones.

In fact, under such a condition, the fingers are bent, with respect to the palm, beyond an allowable bending angle.

Likewise a falling skier may also be subjected to luxations and fractures at the region of his/her wrist.

SUMMARY OF THE INVENTION

Accordingly, the aim of the present invention is to overcome the above mentioned drawbacks, by providing a glove construction, including means for protecting the ligaments, articulations and bones of the hand, which is suitable to properly protect the hand ligaments, articulations and bones while preventing in the case of a violent impact against the soil, the fingers from being bent beyond a natural allowable bending angle, so as to reduce the impact force against the wrist.

Within the scope of the above mentioned aim, a main object of the present invention is to provide such a glove construction which, while including very efficient protecting means, can be easily worn likewise a conventional glove and which, moreover, does not hinder the wearer during the conventional use time.

Another object of the present invention is to provide such a glove construction which, owing to its particular constructional feature, is very reliable and safe in operation.

Yet another object of the present invention is to provide such a glove construction which can be made starting from easily available elements and materials and which, moreover, is very competitive from a mere economic standpoint.

According to one aspect of the present invention, the above mentioned aim and objects, as well as yet other objects, which will become more apparent hereinafter, are achieved by a glove with means for protecting the ligaments, articulations and bones of an user hand, characterized in that said glove comprises a glove body, therewith there is associated a plate for protecting the palm of the hand, at the proximal region of the forearm, said plate being provided, at one end portion thereof, with an annular element encompassing the attachment region of the hand thumb, to said plate there being moreover articulated a shield, which can be engaged with the forearm, tie-straps being moreover provided for connecting the fingers of the glove with said plate.

BRIEF DESCRIPTION OF THE DRAWINGS

Further characteristics and advantages of the present invention will become more apparent hereinafter from the following detailed disclosure of a preferred, though not exclusive, embodiment of a glove with means for protecting the ligaments and articulations of the hand, which is illustrated, by way of an indicative, but not limitative example, with reference to the accompanying drawings, where:

FIG. 2 illustrates the body of the glove according to the invention;

FIG. 3 is a schematic perspective view illustrating the protective plate and the shield articulated to said protective plate;

DESCRIPTION OF THE PREFERRED EMBODIMENT

Figure 1:
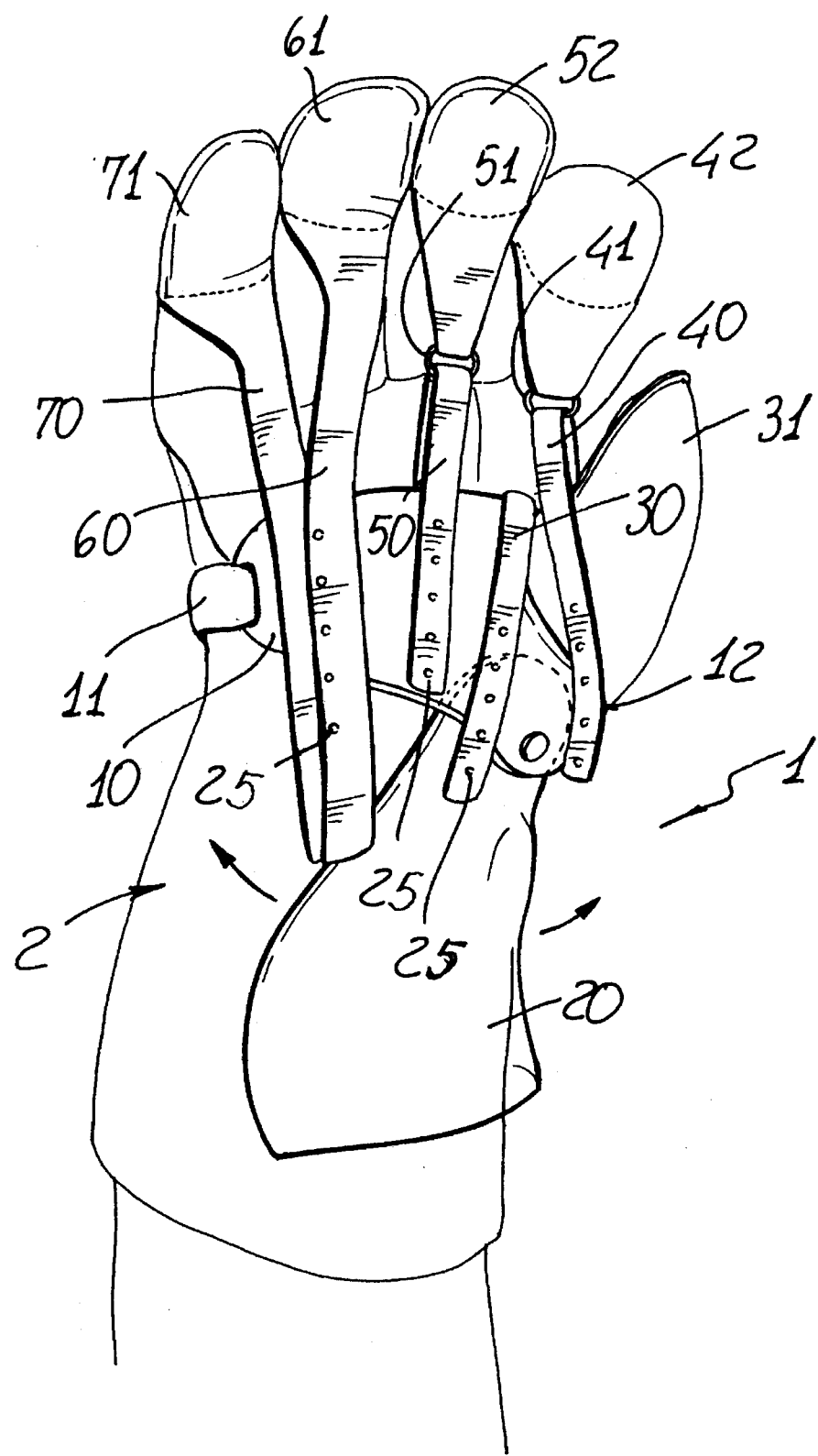
FIG. 1 illustrates the glove construction according to the present invention, by a perspective view.
Figure 4:
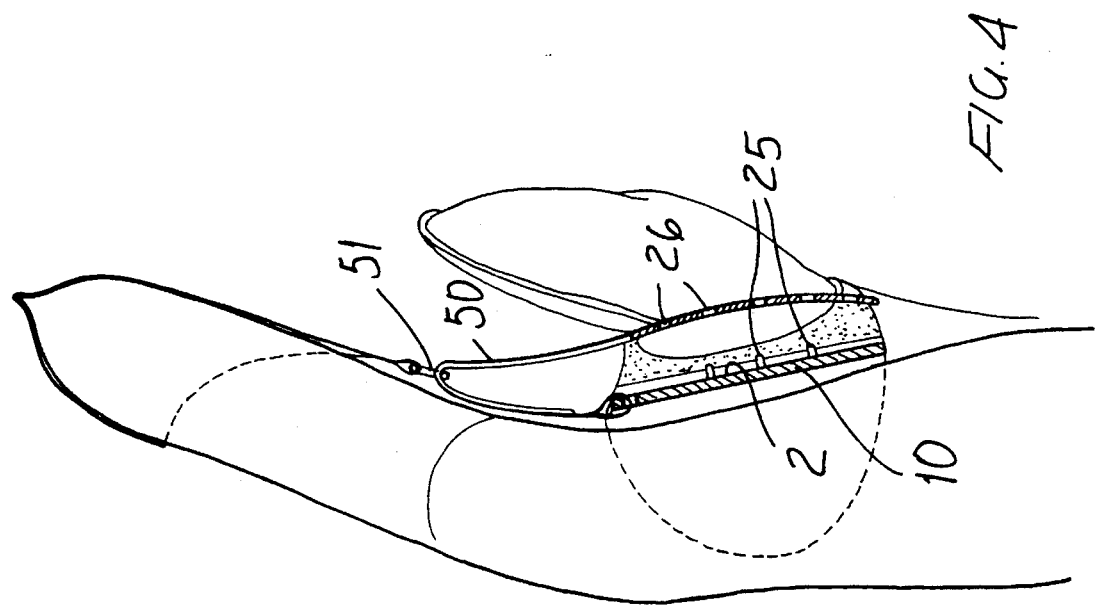
FIG. 4 is a cross-sectional view illustrating, on the body of the glove, a type of connection of the tie-straps.
Figure 5:
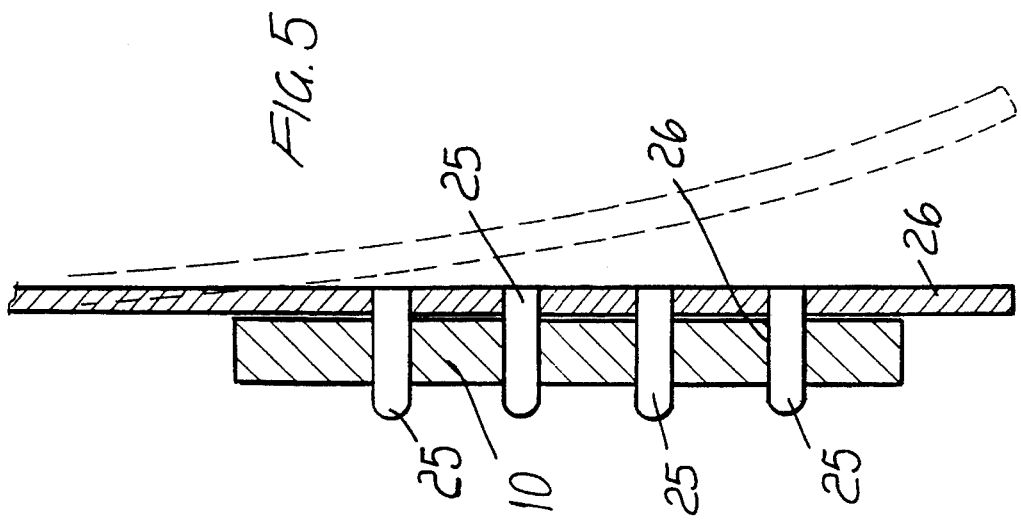
FIG. 5 illustrates, on an enlarged scale, means for connecting the tie-straps to the protective plate.

With reference to the number references of the figures of the drawings, the glove construction, including means for protecting the ligaments, articulations and bones of the hand, according to the present invention, which has been generally indicated at the reference number 1, comprises a glove body 2 which is made of any suitable materials and has a conventional configuration.

At the region of the hand palm and, more specifically, at the proximal region of the forearm, is provided a rigid plate 10 which, if desired, can be connected to the glove by cords 11, affixed to the back part of said glove.

The rigid plate, which has advantageously an anatomic configuration, defines at one end portion thereof, an annular element 12 which is arranged at the attachment region of the hand thumb.

To the protective plate 10, in particular, is articulated a substantially rigid shield 20 which is connected to the leading portion of the forearm and operates, in cooperation with the protective plate, as an element for protecting the articulation between the hand and forearm, so as to prevent, in the case of a violent impact, luxations of the articulations or breakages of the bones.

Another important feature of the present invention is that there are provided tie-strap elements connecting the fingers of the glove body with said protective plate, so as to prevent possible lesions of the ligaments, in the case of an impact, as well as possible lesions of the hand articulations and finger bones.

According to a preferred though not limitative embodiment, there is provided a first tie-strap element 30 which is affixed near the tip portion of the thumb 31 of the glove body and which encompasses the annular element and is connected to the protective plate.

The means for connecting the tie-strap elements and protective plate can be made in several manners.

According to a preferred, though not limitative, embodiment, there are provided pegs 25 distributed on the tie-strap and which can be engaged in holes 26 provided on the protective plate, so as to allow the tie-strap to have a desired useful length.

Moreover, there is provided a second tie-strap element 40, extending from the body of the protective plate and engaging with a first small ring element 41 provided at the tip of the forefinger 42 of the glove body, to be connected to the protective plate 10.

Likewise, there is provided a third tie-strap element 50, also extending from the protective plate 10 and which can be engaged in a second small ring element 51, defined on the middle finger 52 of the glove body, to be connected to the protective plate.

A fourth tie-strap element 60 extends from the ring-finger 61 of the glove body and ends with a strip, also provided with pegs 25 for engaging in the holes 26 of the protective plate.

Furthermore, at the little finger of the glove body there is provided a fifth tie-strap element 70, extending from the little finger 71 of the glove body and ending with a strip, provided with pegs 25 for engaging in the holes 26 of the protective plate.

With the disclosed arrangement, at the palm of the hand there are provided a plurality of tie-strap elements which, in the case of a violent impact against the soil, will absorb any force tending to bend the hand fingers, with respect to the hand palm, so as to properly protect the hand ligaments, articulations and bones.

The provision of the flexible tie-strap elements allows the user to freely bend his/her fingers with respect to the hand palm, thereby allowing the hand to be freely used for example for the ski, while providing a proper protection against possible violent impacts.

In fact, the impact stresses will be mainly discharged, through the tie-strap elements, on the protective plate which, being substantially rigid, will absorb the impact force, while preventing the hand ligaments, articulations and bones from being damaged.

From the above disclosure it should be apparent that the invention fully achieves the intended aim and objects.

In particular, the fact is to be pointed out that a glove construction has been provided which, while being adapted to be easily worn by the user, provides a very good protection both for the hand ligaments and for the hand articulations and bones.

The invention as disclosed is susceptible to several modifications and variations all of which will come within the scope of the inventive idea.

Moreover, all of the details can be replaced by other technically equivalent elements.

In practicing the invention, the used materials, as well as the contigent size and shapes, can be any, depending on requirements.

We claim:

1. A glove with means for protecting the ligaments, articulations and bones of an user hand, said glove having glove thumb, forefinger, middle ring and small fingers and comprising a glove body, a plate for protecting the palm of the hand connected to said glove body, said plate being provided, at one end portion thereof, with an annular element encompassing a bottom region of the hand thumb, to said plate being moreover pivotally connected a forearm engaging shield, tie-straps being moreover provided for connecting said fingers of said glove with said plate, said tie-straps having each a hole through a free end portion thereof.

2. A glove, according to claim 1, wherein said plate and shield are substantially rigid.

3. A glove, according to claim 1, wherein said plate and shield have a substantially anatomic configuration.

4. A glove, according to claim 1, wherein said glove further includes cord elements for connecting said plate at a set position, said cord elements being connected at a back portion of the glove body.

5. A glove, according to claim 1, wherein said tie-strap elements comprise a first tie-strap, extending from the thumb of the body of the glove and encompassing said annular element, said first tie-strap being removably connected to said plate.

6. A glove, according to claim 1, wherein said glove further comprises a second tie-strap extending from said plate and engaging in a ring element supported by said forefinger of said body of the glove and removably connected to said plate.

7. A glove, according to claim 1, wherein said glove further comprises a third tie-strap, extending from said plate and engaging in a further ring element supported by said middle finger of said body of the glove and removably connected to said plate.

8. A glove, according to claim 1, wherein said glove further comprises a fourth tie-strap, extending from said ring finger or said body of the glove and removably connected to said plate.

9. A glove, according to claim 1, wherein said glove further comprises a fifth tie-strap extending from said small finger of said body of said glove and connected to said plate.

10. A glove, according to claim 1, wherein said plate and tie-straps are connected by pegs formed on said plate and removably engaged in said holes formed at said free end portions of said tie-straps.

* * * * *